US00PP29577P3

(12) United States Plant Patent
Probasco et al.

(10) Patent No.: US PP29,577 P3
(45) Date of Patent: Aug. 7, 2018

(54) HOP PLANT NAMED 'HBC 438'

(50) Latin Name: *Humulus lupulus*
Varietal Denomination: HBC 438

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 15/330,748

(22) Filed: Nov. 1, 2016

(65) Prior Publication Data

US 2017/0127589 P1 May 4, 2017

Related U.S. Application Data

(60) Provisional application No. 62/285,576, filed on Nov. 2, 2015.

(51) Int. Cl.
*A01H 5/00* (2018.01)

(52) U.S. Cl.
USPC ..... Plt./236
CPC ..... *A01H 5/00* (2013.01)

(58) Field of Classification Search
USPC ..... Plt./236
CPC ..... A01H 5/00
See application file for complete search history.

(56) References Cited

PUBLICATIONS https://www.fivebladesbrewing.com/neomexicanus-hop-review-hbc-438/; Aug. 3, 2015; 15 pages.*

* cited by examiner

*Primary Examiner* — Kent L Bell
(74) *Attorney, Agent, or Firm* — Svendsen Legal, LLC

(57) ABSTRACT

A new hop plant named 'HBC 438' is disclosed. 'HBC 438' is used for its exceptional and unique aromatic qualities.

6 Drawing Sheets

Genus and species: *Humulus lupulus*.
Variety denomination: 'HBC 438'.

STATEMENT REGARDING FEDERALLY SPONSORED RESEARCH OR DEVELOPMENT

None

BACKGROUND OF THE INVENTION

'HBC 438' is a product of a controlled breeding program carried out by the inventors in the Yakima Valley of Washington State. 'HBC 438' was one of several seedlings resulting from an open pollination made in 2010 with female parent 'YCR 123' (unpatented). A single plant of 'HBC 438' was selected in 2007, and was asexually reproduced via softwood cuttings in a greenhouse near Toppenish, Wash. In 2008 'HBC 438' was expanded to 30 plants, which were planted in the area of Toppenish, Wash. The plants were observed and evaluated for several years, and in 2012 a 1 acre test plot of 'HBC 438' was established in the area of Toppenish, Wash. Throughout several generations of asexual propagation, 'HBC 438' has been observed to retain its distinctive characteristics and remain true to type.

COMPARISON OF 'HBC 438' TO PARENT PLANT AND COMPARISON CULTIVAR

Table 1. below, sets forth some of the distinguishing characteristics of 'HBC 438' as compared to its female parent 'YCR 123', and to the 'Chinook' cultivar as a closely comparable cultivar.

TABLE 1

| | INSTANT CV. 'HBC 438' | FEMALE PARENT 'YCR 123' | COMPARISON CV. 'CHINOOK' |
|---|---|---|---|
| Alpha (% of cone weight) | 14.5 | 2.9 | 11.5-15 |
| Beta (% of cone weight) | 5.8 | 7.81 | 3-4 |
| Co-humulone (% of alpha acids) | 22.6 | 40.1 | 27-31 |
| Total Oil (mL/100 g) | 2.95 | 1-1.6 | 1-2.5 |
| Aroma Profile | peachy, stone fruit, tropical, cedar, and coconut | not available | grapefruit, spice, and pine |

BRIEF DESCRIPTION OF THE PHOTOGRAPHS

Figure 1:
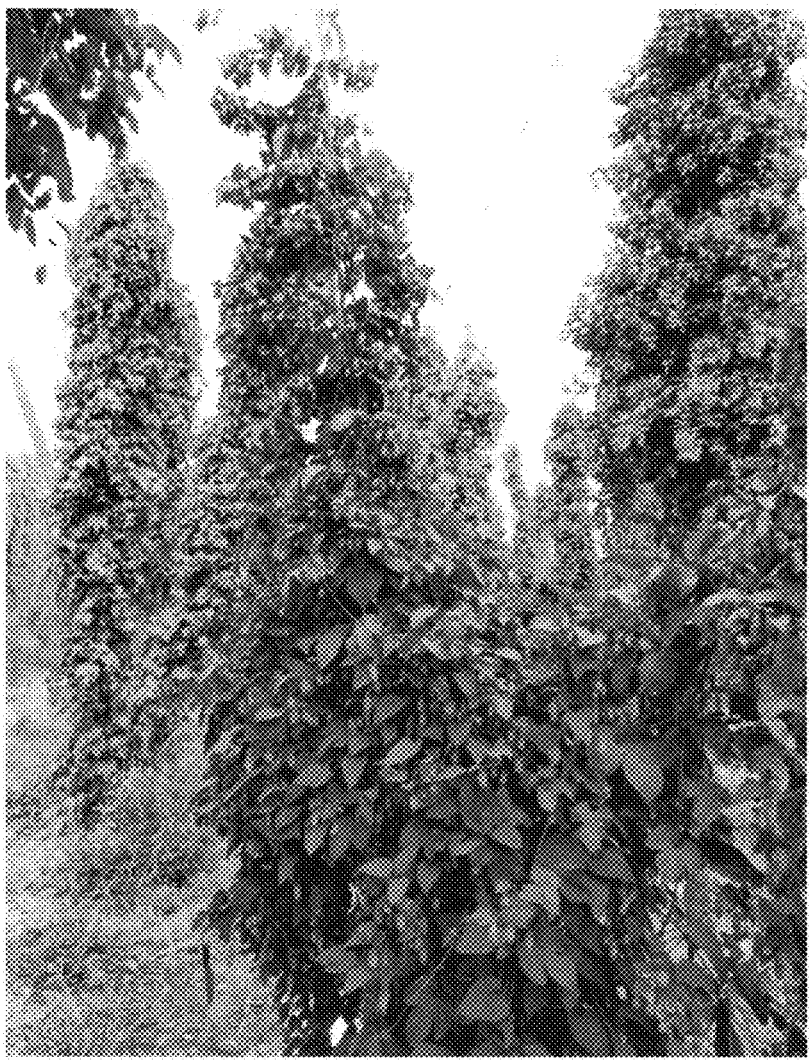
FIG. 1 illustrates a mature 'HBC 438' hop plant grown on a trellis.
Figure 2:
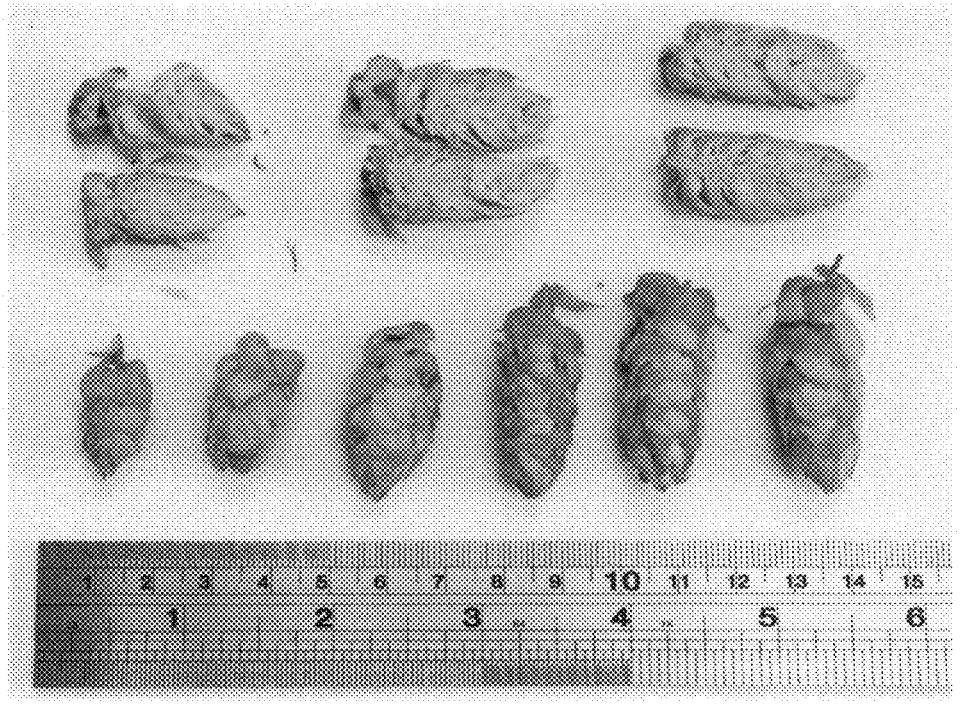
FIG. 2 illustrates whole cones and cross sections of cones of the 'HBC 438' hop plant.
Figure 3:
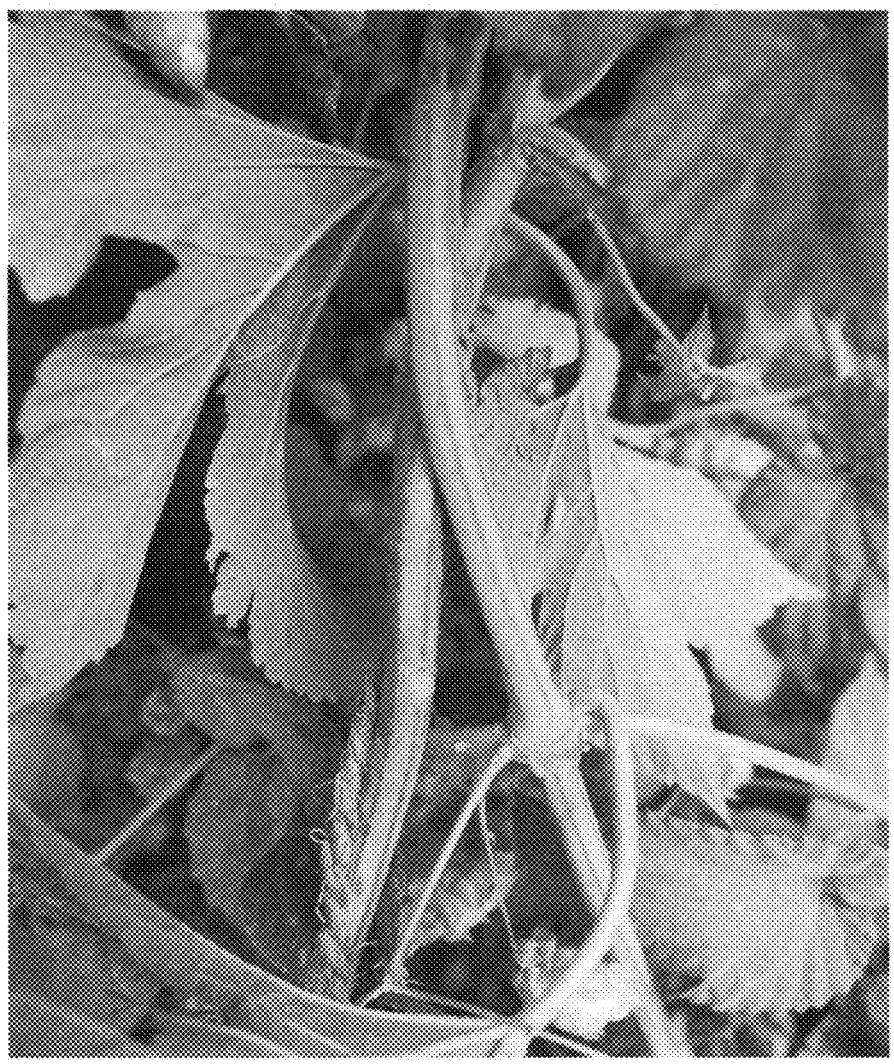
FIG. 3 illustrates the bine of a mature 'HBC 438' hop plant.
Figure 4:
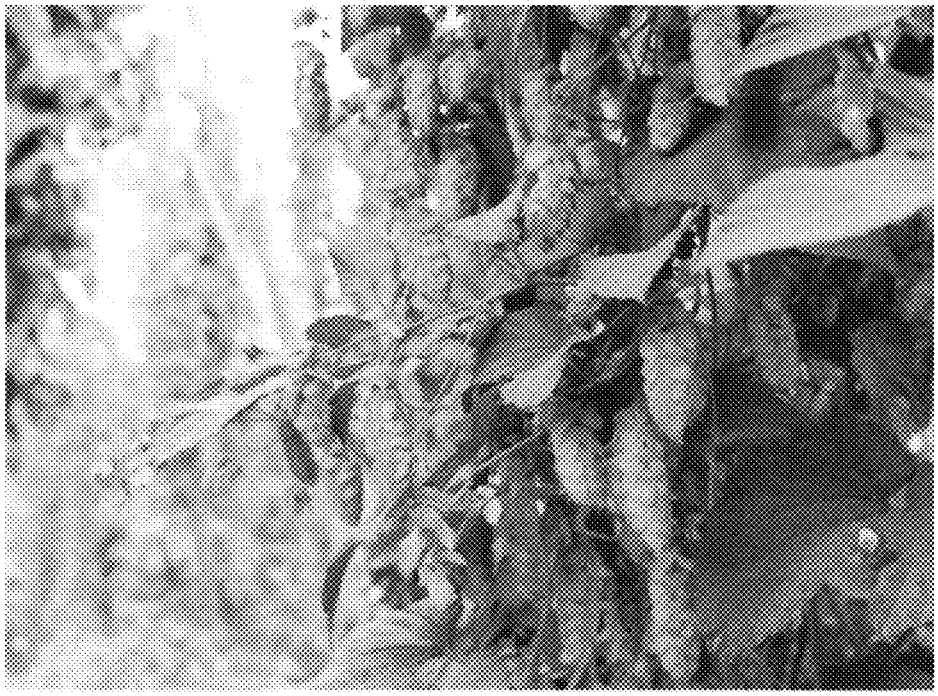
FIG. 4 illustrates cones on a mature 'HBC 438' hop plant.
Figure 5:
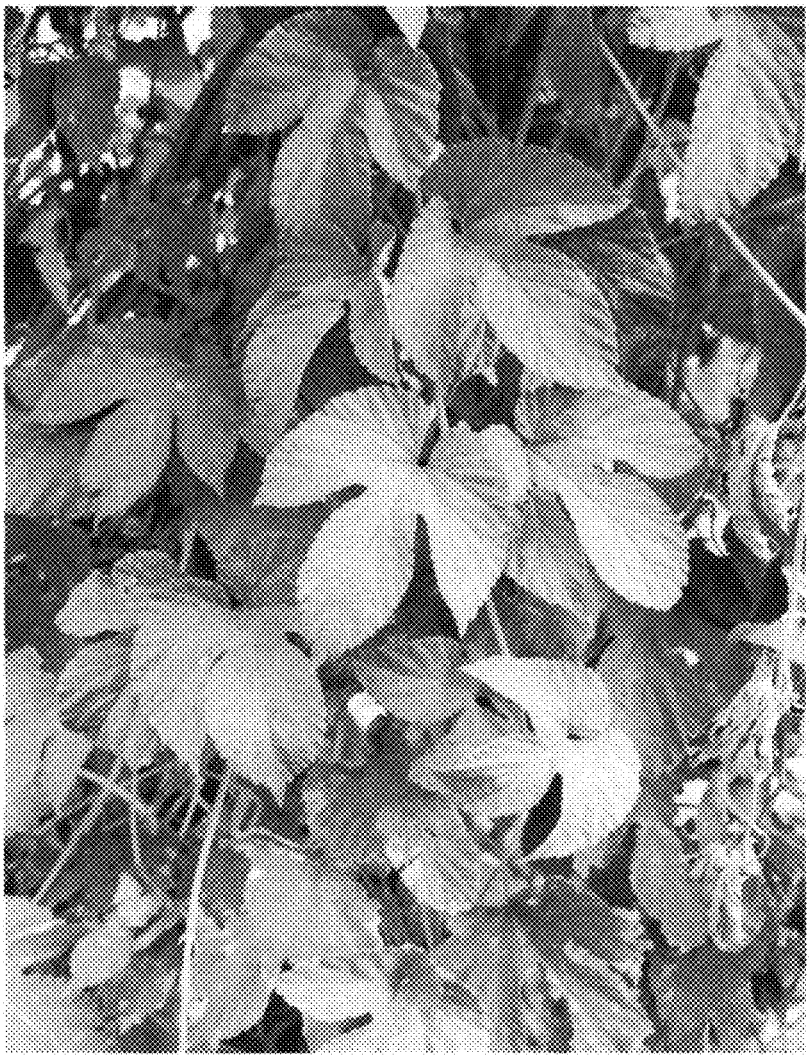
FIG. 5 illustrates leaves on a mature 'HBC 438' hop plant.
Figure 6:
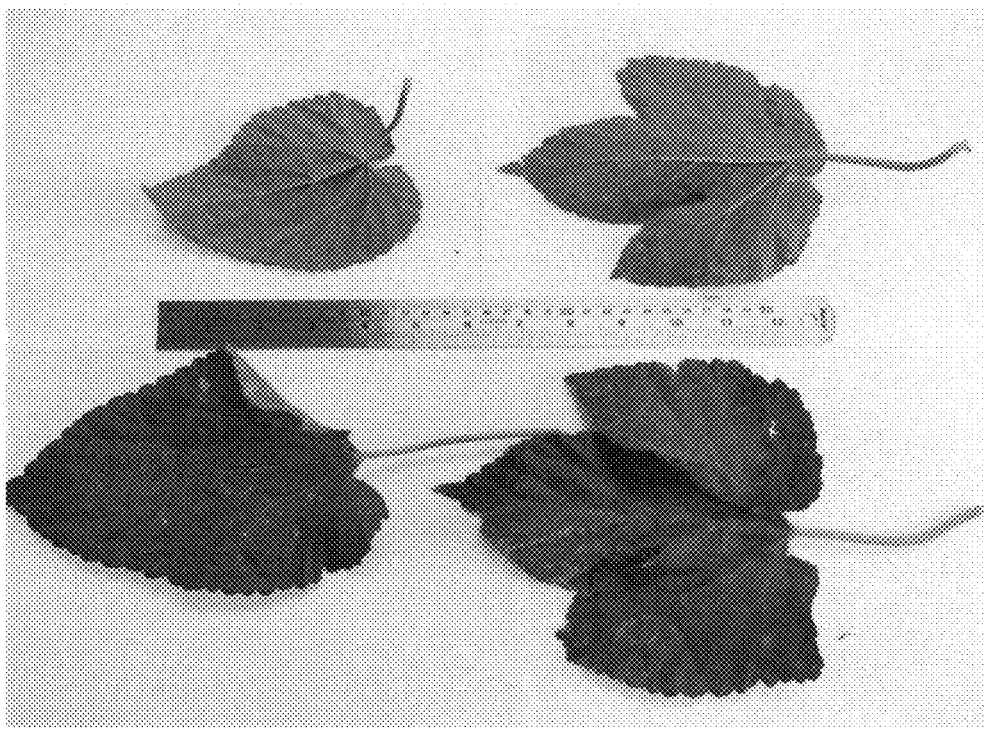
FIG. 6 illustrates leaves of the 'HBC 438' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2007-2015 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on The Royal Horticultural Society Colour Chart.

Ploidy: Diploid (2n=2x).

Sex: Female.

Disease/pest resistance/susceptibility: Resistant to powdery mildew. Reaction to other common hop diseases unknown, none observed to date.

Use: Brewing beer and ale.

Harvest date: September (during 2008 to 2015 growing seasons at Toppenish, Wash.).

Crop yield: Approximately between 1,800 lbs per acre and 2,300 lbs per acre.

Plant shape: Climbing bine, columnar growth.

Quality characteristics (averages):

*Alpha acid* (*as % of cone weight*).—14.5%.
*Beta acid* (*as % of cone weight*).—5.8%.
*Cohumulone* (*as % of alpha acids*).—22.6%.
*Storageability* (*% loss*).—32%.

Oil analytical characteristics (averages):

*Total oil* (*ml/100 g of cones*).—2.95 ml.
*A-pinene.*—0.11% Total Oil.
*B-pinene.*—0.90% Total Oil.
*Myrcene.*—60.75% Total Oil.
2-*methyl-butyl isobutyrate.*—1.92% Total Oil.
*Limonene.*—0.26% Total Oil.
*Linalool.*—0.41% Total Oil.
*Caryophyllene.*—10.47% Total Oil.
*Farnesene.*—0.61% Total Oil.
*Humulene.*—10.05% Total Oil.
*Citral.*—0.99% Total Oil.
*Geranyl acetate.*—0.04% Total Oil.
*Citronellol.*—1.19% Total Oil.
*Nerol.*—0.15% Total Oil.
*Geraniol.*—0.84% Total Oil.
*B-lonene.*—0.01% Total Oil.

Bine:

*Color.*—Green 144A.
*Stripe present.*—Yes.
*Stripe color.*—Greyed-Purple 185A.
*Stipule direction.*—Up.
*Stipule color.*—Yellow-Green 144A.
*Average number of stipule per bine.*—Two per node.
*Typical and observed bine length.*—Typical bine growth of 18 feet to 20 feet, when grown on a standard eighteen foot trellis.
*Bine diameter.*—11 mm at base; 10 mm at nine feet; 9 mm at terminal end of eighteen feet.

Lateral:

*Color.*—Yellow-Green 144A.
*Typical and observed lateral length.*—84 cm to 134 cm.
*Internode length of laterals.*—11.5 cm to 15.9 cm.
*Lateral diameter.*—3 mm to 6 mm at the base; and 1 mm to 1.5 mm at the terminal end.

Leaf:

*Arrangement.*—Acuminate.
*Shape.*—Palmately Lobed — Cordate.
*Leaf apex descriptor.*—Acuminate.
*Leaf base descriptor.*—Cordate.
*Average length of mature leaf.*—19 cm.
*Average width of mature leaf.*—15 cm.
*Color of mature leaf upper surface.*—Yellow-Green 147A.
*Color of mature leaf lower surface.*—Yellow-Green 147B.
*Color of immature leaf upper surface.*—Yellow-Green 146A.
*Color of immature leaf lower surface.*—Yellow-Green 146B.
*Number of lobes.*—1-3.
*Margin.*—Serrate.
*Serrations per inch.*—4.
*Average petiole length* (*mature*).—9 cm.
*Petiole color.*—Yellow-Green 144A.
*Petiole color at base.*—Yellow-Green 144A.
*Venation.*—Palmate.
*Vein color.*—Yellow-Green 146C.

Cone:

*Avg. length.*—32 mm.
*Avg. diameter.*—14 mm.
*Avg. weight.*—650 mg to 1100 mg.
*Pickability.*—Good.
*Bract tip color* (*both surfaces*).—Yellow-Green 144A.
*Bract inner surface color.*—Yellow-Green 144A.
*Bract outer surface color.*—Green 145A.
*Bract base color* (*both surfaces*).—Yellow-Green 145A.
*Bract margin.*—Entire.
*Bract base.*—Rounded.
*Bracteole color* (*both surfaces*).—Yellow-Green 144A.
*Bracteole typical length.*—12.5 mm.
*Bracteole typical width.*—7.8 mm.
*Cone shape.*—Ovate.
*Bract shape.*—Ovate.
*Bract tip shape.*—Acuminate-Mucronate.
*Bract tip position.*—Loosely Appressed — Recurved.
*Bracteole shape.*—Ovate.

What is claimed:

1. A new and distinct Hop plant as illustrated and described herein.

* * * * *